(12) United States Patent
Jones et al.

(10) Patent No.: US 8,466,686 B2
(45) Date of Patent: Jun. 18, 2013

(54) TEST PATCH SYSTEM

(75) Inventors: Galvin Jones, Louisville, KY (US);
Joseph E. Yates, Crestwood, KY (US)

(73) Assignee: Louisville Solutions Incorporated, Louisville, KY (US)

( * ) Notice: Subject to any disclaimer, the term of this patent is extended or adjusted under 35 U.S.C. 154(b) by 426 days.

(21) Appl. No.: 12/940,180

(22) Filed: Nov. 5, 2010

(65) Prior Publication Data
US 2011/0192238 A1    Aug. 11, 2011

Related U.S. Application Data

(60) Provisional application No. 61/301,920, filed on Feb. 5, 2010.

(51) Int. Cl.
*G01N 27/02* (2006.01)
*G01N 27/06* (2006.01)

(52) U.S. Cl.
CPC ................................. *G01N 27/06* (2013.01)
USPC ....................... 324/439; 73/863.21

(58) Field of Classification Search
USPC .............. 73/866, 863.21; 324/691, 649, 600, 324/438, 439, 451, 453, 71.1
See application file for complete search history.

(56) References Cited

U.S. PATENT DOCUMENTS
2009/0015273 A1*   1/2009  Gossen et al. ................ 324/693

\* cited by examiner

*Primary Examiner* — Peter Macchiarolo
*Assistant Examiner* — Tamiko Bellamy
(74) *Attorney, Agent, or Firm* — Middleton Reutlinger; Alexander P. Brackett

(57) ABSTRACT

A test system for taking a sample of a constituent on a surface utilizing a fluid source includes an upper body and a concomitant mating lower body that includes an aperture in a portion thereof. A central fiber portion and a support extend through upper body aperture to provide a consistent surface for contacting the surface to be tested.

17 Claims, 11 Drawing Sheets

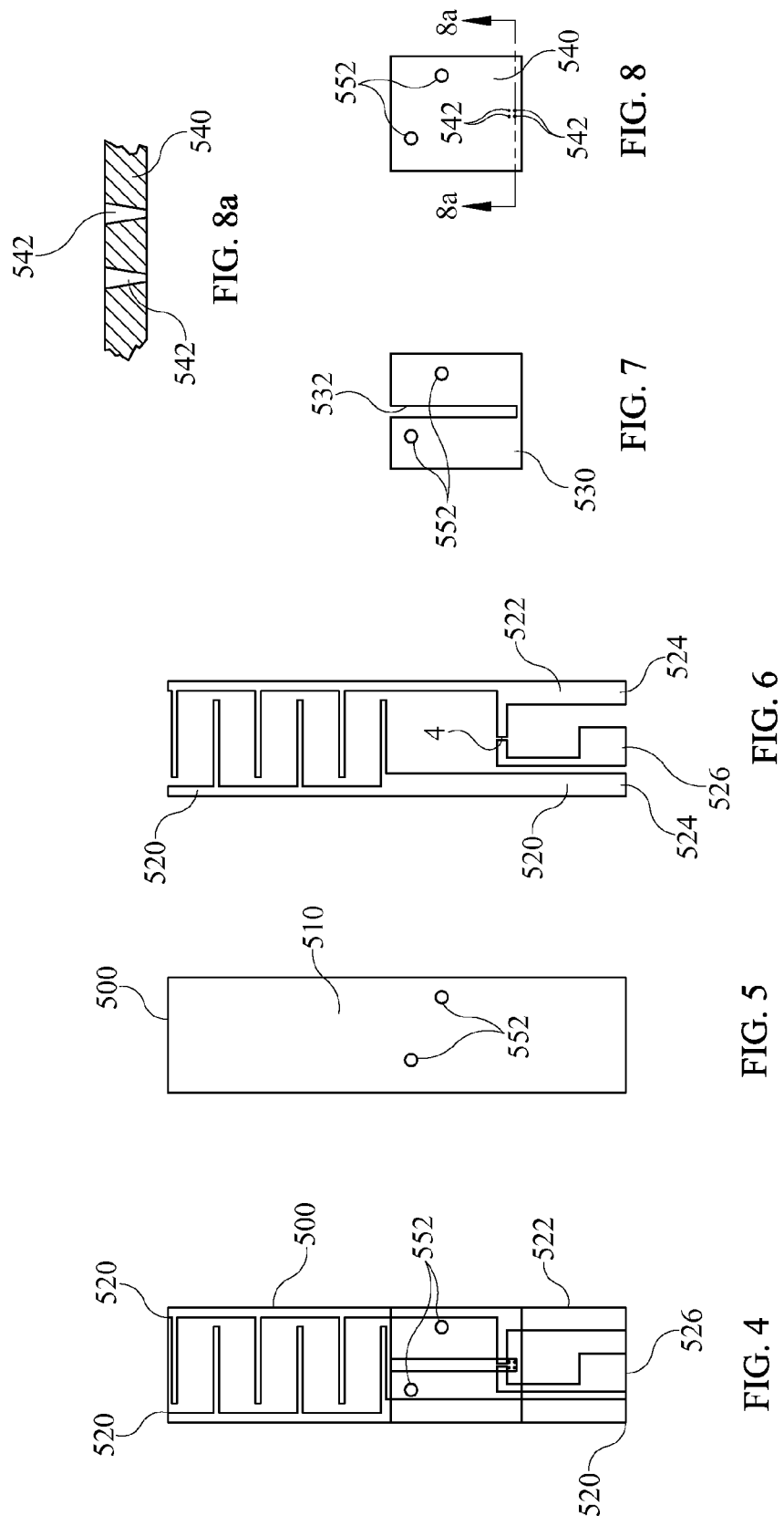

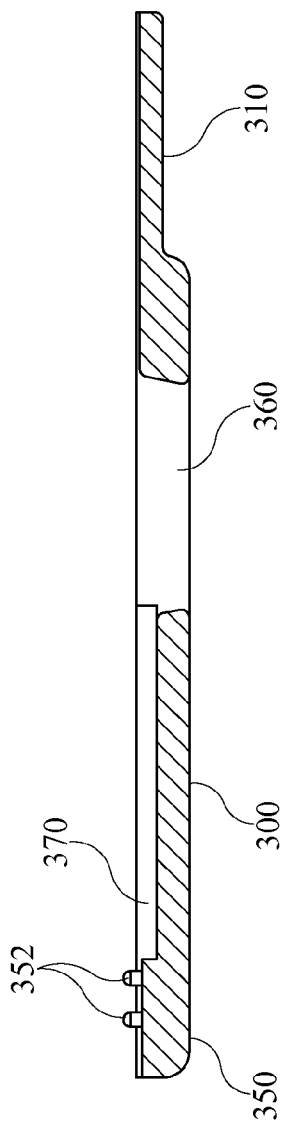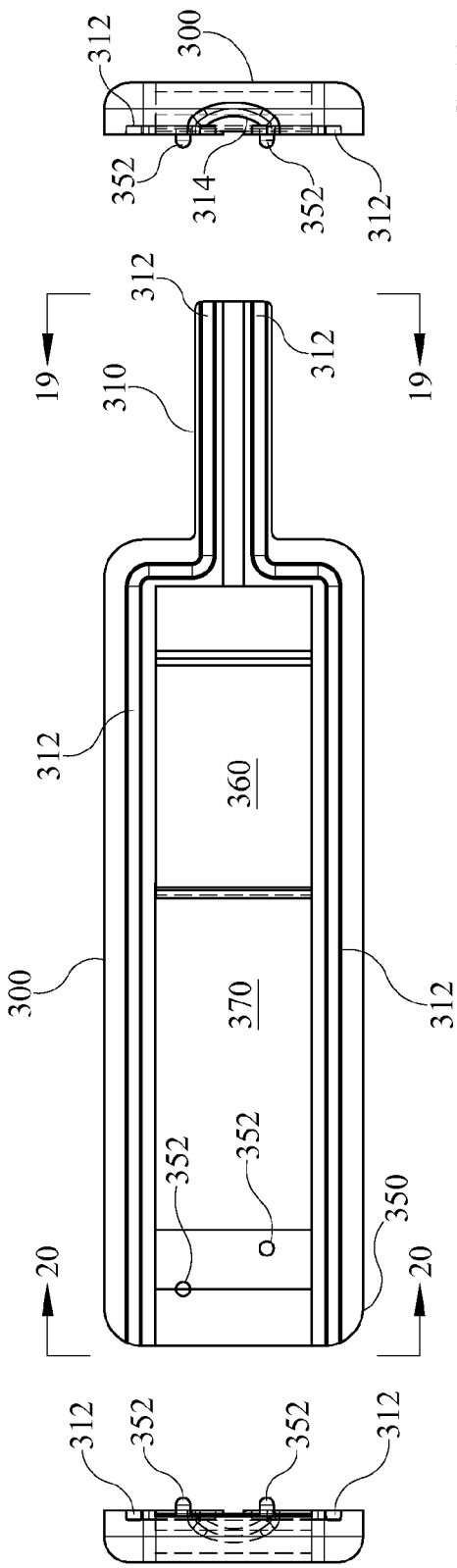

TEST PATCH SYSTEM

CROSS-REFERENCE TO RELATED APPLICATIONS

This application claims the benefit of U.S. Provisional Patent Application Ser. No. 61/301,920 filed Feb. 5, 2010 and entitled "Improved Test Patch System".

The U.S. Government has a paid-up license in this invention and the right in limited circumstances to require the patent owner to license others on reasonable terms as provided for by the terms of contract no N00167-07-C-0008 awarded by the U.S. Department of the Navy.

BACKGROUND OF THE INVENTION

1. Field of the Invention

The present invention relates generally to a system for surface contaminant testing and more specifically to a system and method for testing a surface for at least one measurable property such as pH, the presence of chlorides or similar contaminants, or conductivity as a measure of the efficacy of a surface treatment applied to the surface.

2. Description of the Related Art

In commercial and industrial applications where the treatment of surfaces with protective coatings is required, it is often necessary to test the treated surfaces to determine whether the protective coating has been properly applied. Furthermore, prior to the treatment of, for example, steel surfaces, the surfaces must be thoroughly cleaned of contaminants and salts such as chloride salts so that corrosion doesn't occur under the treated or painted surface. Accordingly, there have been developed various and sundry prior art systems for determining the presence of contaminants of various types on surfaces.

As one example, salt contamination on steel surfaces is a widespread problem in the shipbuilding industry. Salt contamination is typically caused by the proximity of a steel ship to ocean air and water, as well as less obvious causes such as salt treatment of icy roads in proximity to the untreated material. Corrosion can occur quite rapidly after a surface is contaminated, so that surfaces must be cleaned, tested and treated quickly in order to avoid the deleterious effects which will eventually appear when a contaminated surface is treated or coated. Furthermore, painting over a salt contaminated surface will eventually cause failure in immersion service materials such as ballast tanks and the like. Ballast tank failures cause an enormous inconvenience and expense to repair since the ship must be removed from service to correct the problem.

Many prior art surface testing devices for various properties such as salinity, pH, or conductivity are typically complex and labor intensive systems that require a multiplicity of steps in order to accomplish the surface testing. In one popular example, a Bresle patch or sampler has been used as a means for measuring chloride contamination on treated surfaces. The Bresle patch comprises a latex membrane and a foam rubber gasket that creates a water tight sample extraction pocket in contact with a surface when a foam rubber gasket is secured to the surface via an adhesive. The watertight sample extraction pocket is then filled with distilled or deionized water, typically by use of a syringe. After agitating the water by rubbing the patch for a short time period, the water is removed, typically through a syringe or the like and analyzed by chemical reagents for a constituent property such as chloride ion content. The chemical analysis is typically done by using a "kit" supplied with reagents and instructions for use. The extracted water may also be analyzed for other properties such as pH, electrical conductivity, or the presence of chloride ions using conventional known-in-the art meters designed for those purposes. Of course, this method and system is quite complex and requires a great deal of labor and expertise to properly execute. Additionally, due to the complexity it is quite easy to make testing errors and obtain inaccurate data in such a prior art system.

Other methods of testing a surface for a constituent property are also known in the art but each of them also requires a large amount of time and energy to collect and analyze a single sample. In many prior art systems, various syringes, bottles of water and reagents, surface test patches and other equipment must be coordinated and assembled in an inhospitable industrial fabrication environment. These prior art methods are quite disadvantageous when testing large surface areas, since samples must be collected at many points around the area being treated in a short time before surface treatment can proceed.

Accordingly, there is a great need in the art for a system and method of testing for a constituent property on a surface that is both economical and capable of being conducted repeatedly and quickly by a user while yielding consistently accurate results.

SUMMARY OF THE INVENTION

Brief Description of the Drawing Figures

FIG. 4 is an elevation view of a central backplane assembly in accordance with one embodiment of the present invention.

FIG. 5 is an elevation view of a central backplane in accordance with one embodiment of the present invention.

FIG. 6 is an elevation view of a plurality of printed electrodes in accordance with one embodiment of the present invention.

FIG. 7 is an elevation view of a fluid channel spacer in accordance with one embodiment of the present invention.

FIG. 8 is an elevation view of a vent spacer in accordance with one embodiment of the present invention.

FIG. 8a is a cross-sectional view of a vent spacer taken along the line 8a-8a of FIG. 8.

FIG. 17 is an elevation view of a lower body of a test patch system in accordance with one embodiment of the instant invention.

FIG. 18 is a top view of a lower body of a test patch system in accordance with one embodiment of the instant invention.

FIG. 19 is a view of a lower body of a test patch system taken along the line 19-19 of FIG. 18 in accordance with one embodiment of the instant invention.

FIG. 20 is a view of a lower body of a test patch system taken along the line 20-20 of FIG. 18 in accordance with one embodiment of the instant invention.

DETAILED DESCRIPTION OF THE PREFERRED EMBODIMENT(S)

Figure 1:
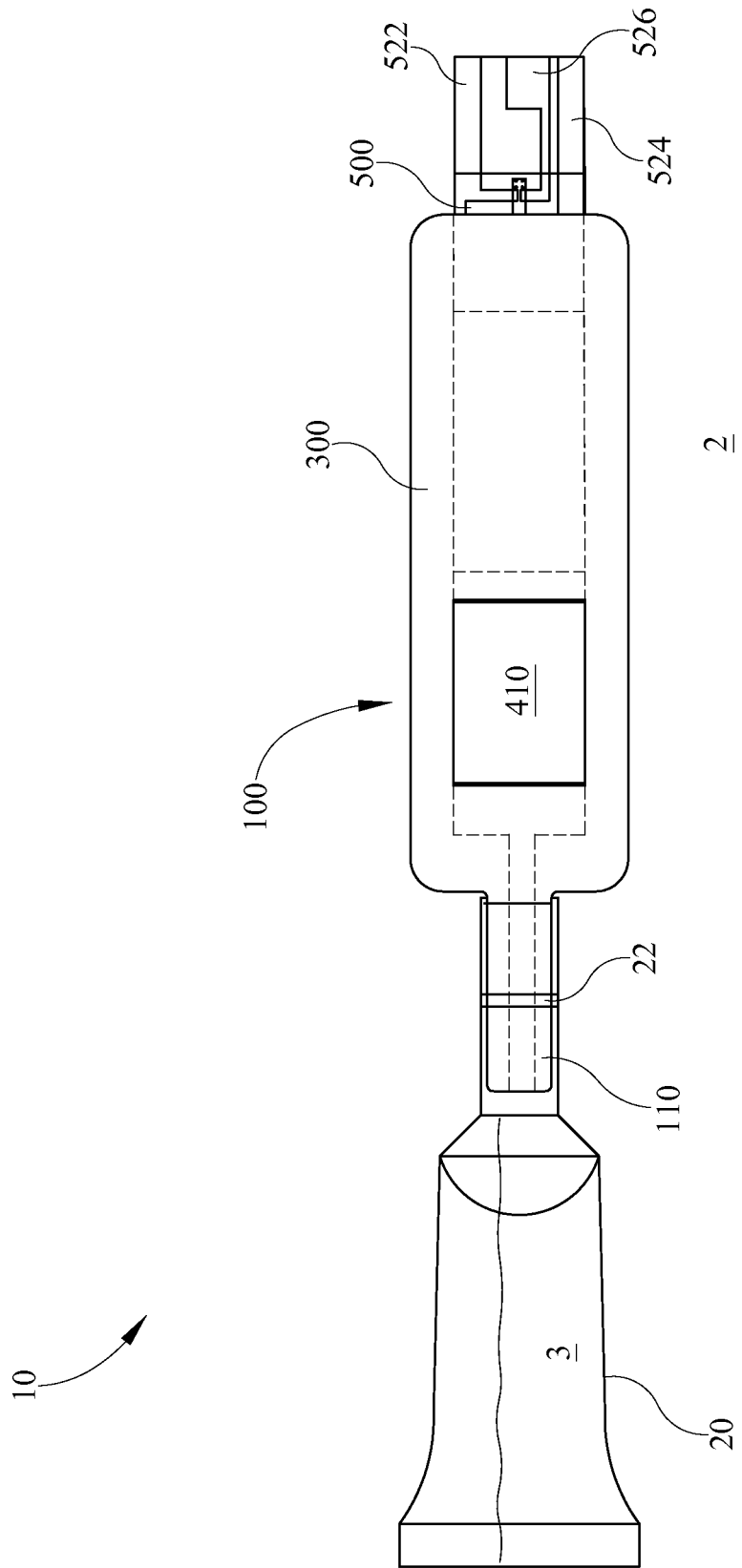
FIG. 1 is a plan view of a test patch system in accordance with one embodiment of the present invention.
Figure 2:
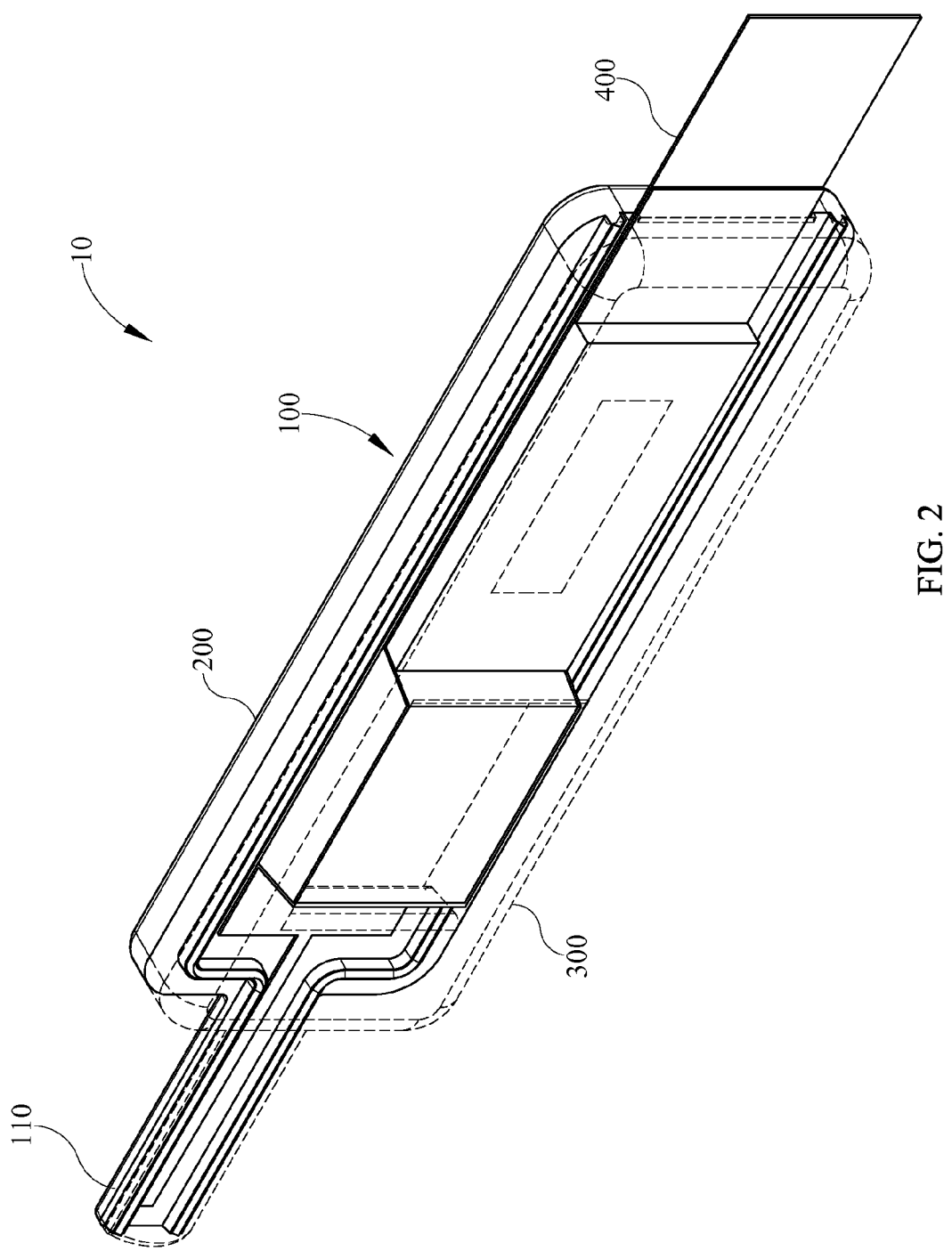
FIG. 2 is an isometric view of a test patch system in accordance with one embodiment of the present invention.
Figure 3:
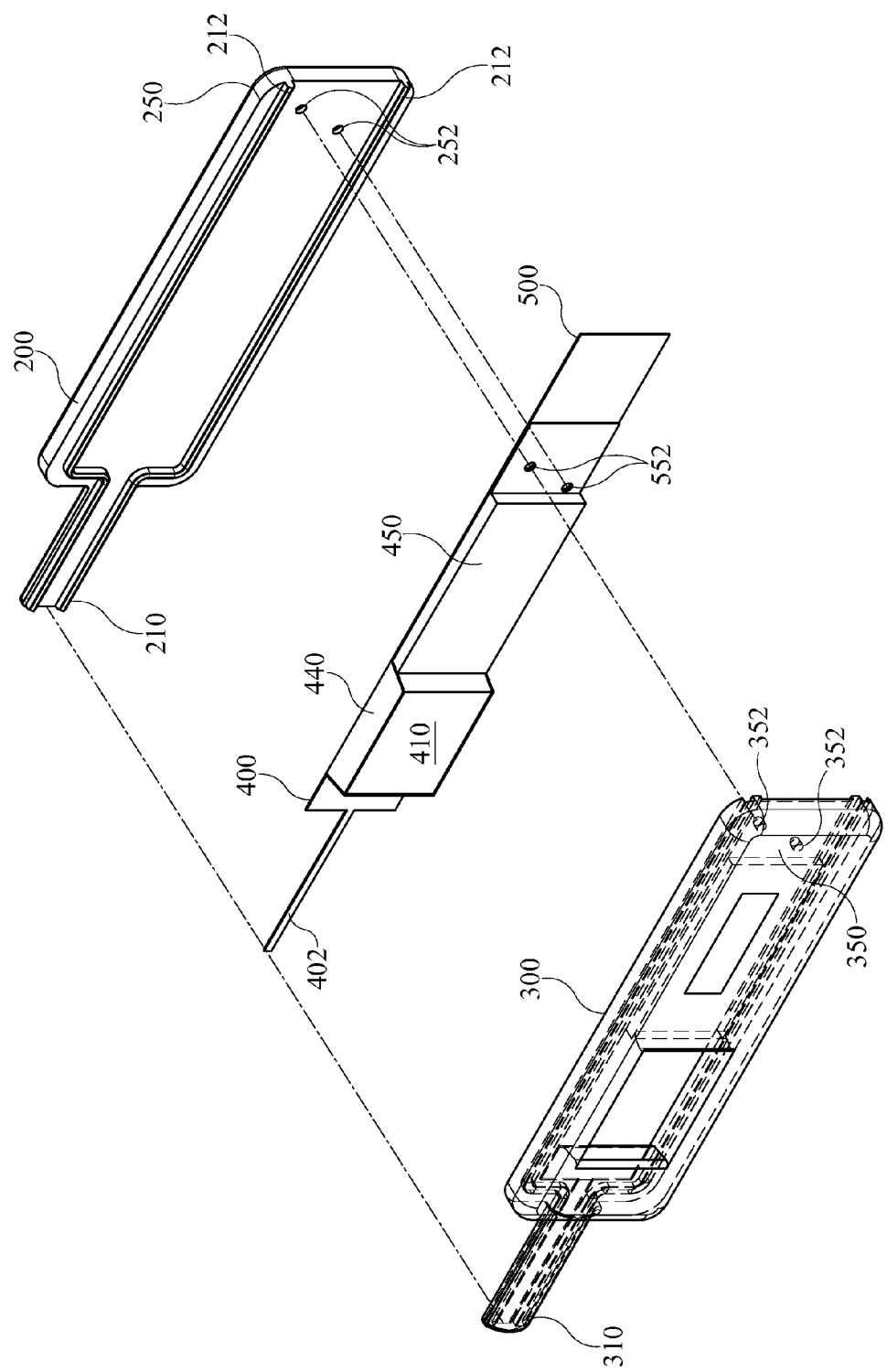
FIG. 3 is an exploded view of a test patch system in accordance with one embodiment of the present invention.
Figure 9:
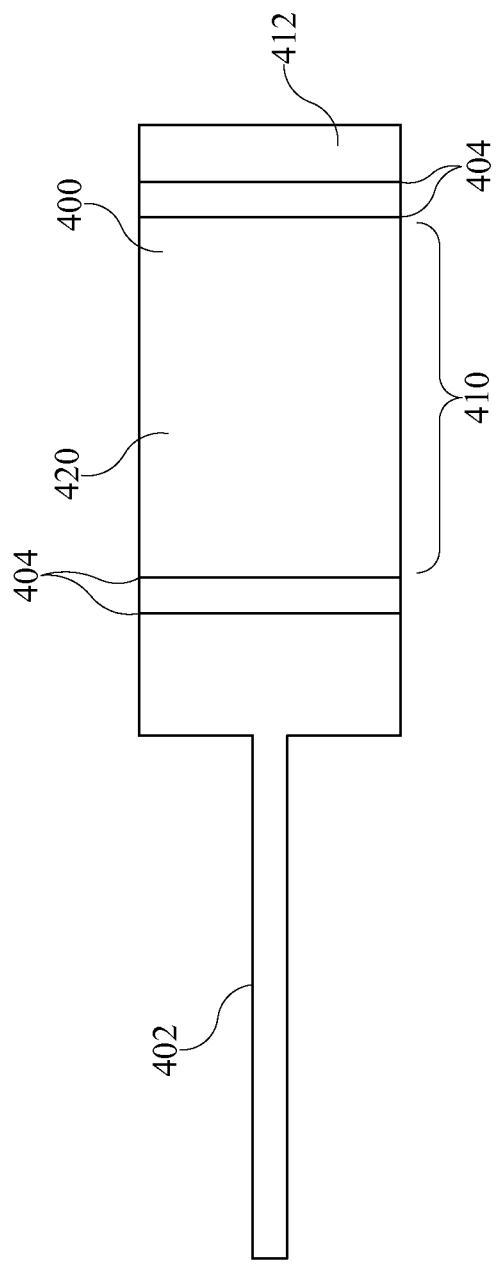
FIG. 9 is a top view of a central fiber portion in accordance with one embodiment of the present invention.
Figure 10:
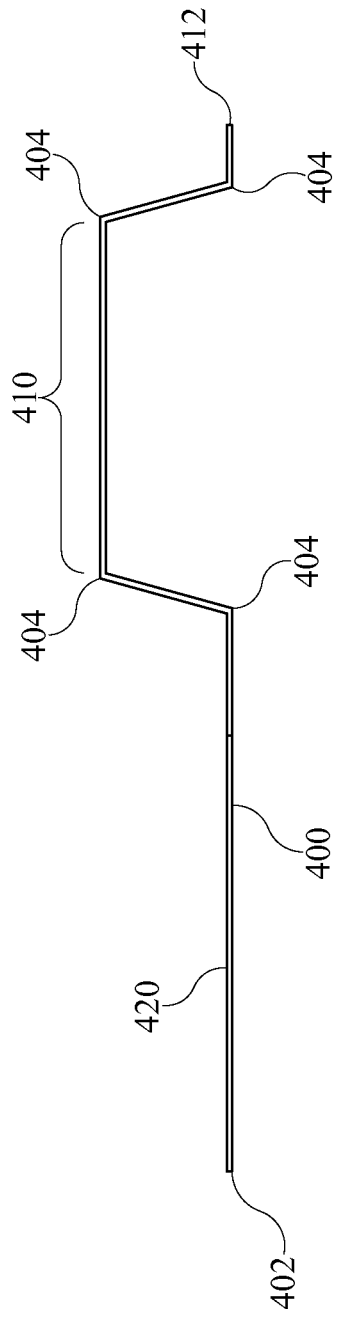
FIG. 10 is an elevation view of a central fiber portion system in accordance with one embodiment of the present invention.

Referring to drawing FIGS. 1-3 and in accordance with a constructed embodiment of the present invention, a test system 10 for testing a surface 2 for the presence of a constituent property comprises a test assembly 100 and an ampoule 20 having a supply of a solvent 3 contained therein. Surface 2 may be any one of a plurality of surfaces on which a constituent may be present. In one exemplary embodiment of the present invention, surface 2 comprises a metal surface, for example a ballast tank of a marine vessel. In this embodiment of the invention 10, the constituent to be detected may be a chloride, which may have deleterious effects on an unpainted or coated surface, and which must be removed prior to painting or coating to prevent failure of the coating over time. Of course, any number of constituents may be detected using system 10 without departing from scope of the present invention.

Ampoule 20 contains a supply of a solvent 3, such as distilled water 3 used to saturate a media for extracting the constituent from surface 2, as will be discussed further below. The distilled water 3 (or other solvent as required by an individual application) contained in ampoule 20 remains separated from test system 100 by a membrane 22 or stopper disposed proximate an outlet area of ampoule 20 until the system is ready to be used. The membrane 22 of ampoule 20 may be pierced by an end portion 110 of assembly 100 when system 10 is ready for use. In one embodiment of the present invention, end portion 110 may be shaped or narrowed to a point to facilitate the piercing of membrane 22. Alternatively, membrane 22 may be designed to rupture to release water into test assembly 100 when membrane 22 is pressurized by, for example, squeezing.

Furthermore, it should be noted that ampoule 20 may be provided as a separate and distinct component to system 10, such that a variety of different ampoules 20 may be employed in conjunction with the invention by inserting ampoule 20 onto or into end portion 110 of assembly 100 without departing from the scope of the present invention.

Test assembly 100 comprises an upper body 200, having a fluid end 210 and a sensor end 250 and a lower body 300, also having a fluid end 310 and a sensor end 350. Upper body 200 and lower body 300 are shaped to enclose a central fiber portion 400 and a central backplane 500 that are employed to direct solvent 3 flow from end portion 110 of assembly 100 to a sensor integrated into central backplane 500, as will be discussed further herein below.

Referring to FIGS. 21-25, upper body 200 is depicted in greater detail. Upper body 200 further comprises a pair of opposed ridges 212 that extend inwardly, toward central backplane 500 when system 10 is assembled. Opposed ridges 212 extend along substantially the entire length of upper body 200, from end portion 210 to sensor end 250. Ridges 212 are designed to protect backplane 500, central fiber portion 400, and other components internal to assembly 100 from radio frequency energy used to weld upper body 200 to lower body 300 during system 10 assembly. Both upper body 200 and lower body 300 may be comprised of a waterproof plastic such as ABS.

Fluid end 210 of upper body 200 may comprise an oval or semi-circular cross-section 214 for providing an open area for solvent 3 to flow into assembly 100. Furthermore, upper body 200 may comprise a plurality of index apertures 252, shown on FIG. 21 as disposed proximate sensor end 250 that mate with complimentary pins provided on lower body 300 to properly align system 10 during assembly.

Referring to FIGS. 16-20 lower body 300 comprises fluid end 310, sensor end 350, and a pair of opposed grooves 312 extending substantially along the entire length of lower body 300, from fluid end 310 to sensor end 350. Grooves 312 mate with complementary ridges 212 of upper body 200 and lower body 300 whereupon they are ultrasonically welded together utilizing known RF welding techniques. Ridges 212 both engage grooves 312 to accurately position upper body 200 and lower body 300 with respect to each other and act to deflect RF energy away from the interior of assembly 100, thereby protecting central backplane 500 and concomitant assembly components from excess heat created by the ultrasonic welding process.

As best seen in FIG. 19 fluid end 310 of lower body 300 may comprise an oval or semi circular cross-section 314 which, when mated with fluid end 210 of upper body 200, provides a channel or path for solvent 3 to flow into assembly 100. Additionally, lower body 300 comprises a plurality of index pins 352 that are positioned to engage complementary index apertures 252 when upper 200 and lower 300 bodies are assembled.

Lower body 300 further comprises an aperture 360 in said body proximate fluid end 310 through which central fiber portion 400 may be positioned, as discussed further herein below. Aperture 360 is generally shaped to conform to an extraction region of central fiber portion 400, as discussed further below. Lower body 300 additionally includes a solvent reservoir 370, into which fluid or solvent 3 flows and is collected for testing as it advances through test assembly 100. As depicted in FIGS. 17 and 18 reservoir 370 is defined as a shallow rectangular depression within lower body 300, between aperture 360 and index pins 352.

Referring to FIGS. 4-8, and in accordance with a constructed embodiment of the invention central backplane 500 may comprise a relatively flat, thin waterproof substrate 510, such as a polyester film plastic that provides a platform for a pair of spaced electrodes 520, 522 that are disposed on substrate 510. Each electrode 520, 522 includes an end 524 that extends out of sensor ends 250, 350 of test assembly 100. A test finished electrode 526 is further provided to indicate when the test for a given constituent is complete. As seen in FIG. 6, test finished electrode 526 is disposed very closely to electrode 522, such that a small space 4 separates them. This feature of the invention provides the ability for solvent 3 to flow into space 4, thereby completing an electrically conductive path between electrodes 522 and 526 and thus providing a "test finished" signal to a reader module (not shown). Electrodes 520, 522 and substrate 510 form a sensor or backplane 500 that may be provided with an electrical signal by a test meter (not shown), that may thus be monitored to test for the presence or a constituent by measuring the strength of an electrical signal or current provided between electrodes 520, 522. Additionally, in an alternative embodiment of the invention, electrodes 520, 522 may be printed or deposited directly onto backplane 500 thereby enhancing ease of assembly and reducing material costs.

Central backplane 500 further includes a plurality of index apertures 552 therein for engaging index pins 352 of lower body 300 upon assembly. Central backplane 500 may further comprise a fluid spacer 530 having a fluid channel 532 therein that extends substantially through fluid spacer 530. Fluid spacer 530 is disposed on central backplane 500 proximate sensors 520, 522 ends 524 so that solvent 3 flows through fluid channel 532 and provides an electrically conductive path between electrode 522 and test finished electrode 526, thereby permitting a user to know when a sufficient amount of solvent 3 has flowed through test assembly 100 to provide a completed test.

Central backplane 500 may additionally comprise a vent spacer 540, that may also be comprised of a waterproof plastic material, for example a polyester film material, having a plurality of microscopic holes 542 therein that are sized to permit the flow of air through vent spacer 540 while prohibiting the flow of water. Holes 542 may, for example, have a diameter of 0.004". Vent spacer 540 may be placed over fluid spacer 530 so that fluid spacer 530 is disposed between backplane 500 and vent spacer 540. Furthermore, vent spacer 540 is positioned such that holes 542 are in fluid communication with fluid channel 532, thereby providing a vent for encouraging solvent 3 flow through test assembly 100.

Both vent spacer 540 and fluid spacer 530 include a plurality of index apertures 552 that align with index apertures 552 of central backplane 500 when vent spacer 540, fluid spacer 530 and backplane 500 are properly assembled. Each of these apertures 552 are then engaged by index pins 352 to properly align backplane 500, fluid spacer 530 and vent spacer 540 within test assembly 100. This feature of the invention provides for a repeatable, consistent test assembly 100 wherein all components are precisely aligned once assembled.

Referring to FIGS. 9-13 central fiber portion 400 comprises a shaped fiber layer 420 that, in an exemplary embodiment is made of fibrous material for transporting solvent 3 through test assembly 100 to central backplane 500 electrodes 520, 522. Central fiber portion 400 includes an elongated narrow capillary portion 402 that transitions into an extraction region 410 that extends or is positioned through aperture 360 of lower body 300, thereby contacting surface 2 for constituent testing. In one embodiment of the present invention, capillary portion 402 and extraction region 410 comprise one continuous fiber material piece, thereby providing a continuous, uninterrupted flow path for solvent 3 from ampoule 20 through fiber portion 400. Additionally, fiber portion 400 extraction region 410 terminates in an end portion 412 that extends into solvent reservoir 370 of lower body 300, thereby delivering solvent 3 that has flowed from ampoule 20 through capillary portion 402 and extraction region 410, into reservoir 370. As best seen in FIG. 3, capillary portion 402 is shaped to conform generally with the shape of fluid ends 210, 310 of upper 200 and lower 300 bodies between ridges 212 and grooves 312 thereof.

Central fiber portion 400 may comprise a plurality of materials that are capable driving the capillary flow of solvent 3 through fiber portion 400 while simultaneously extracting salts or other constituents from surface 2 in contact with extraction region 410. In one embodiment of the present invention, fiber portion 400 comprises a layer or layers of absorbent fiber material that provides a flow transport mechanism from sample surface 2 to collect a constituent sample. Other exemplary fiber portion 400 materials include various sponge-like materials, felt fiber mats, paper fiber mats, or spun fiber mats made from synthetic or natural materials that provide a suitable capillary force or action to draw the solvent 3 across extraction region 410 while keeping solvent 3 in continuous contact with surface 2 and that are suitable for conforming to rough uneven surfaces.

Figure 13:
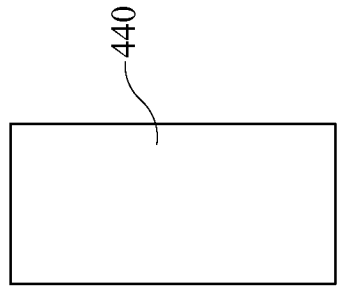
FIG. 13 is a side view of a support taken along the line 13-13 of FIG. 12 in accordance with one embodiment of the instant invention.
Figure 12:
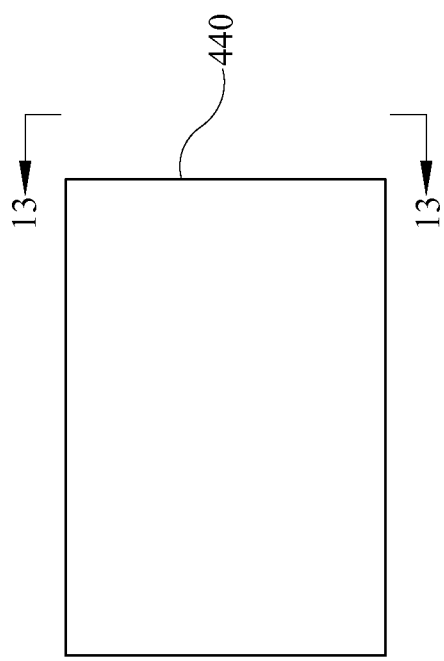
FIG. 12 is a top view of a support taken along the line 12-12 of FIG. 11 in accordance with one embodiment of the instant invention.
Figure 11:
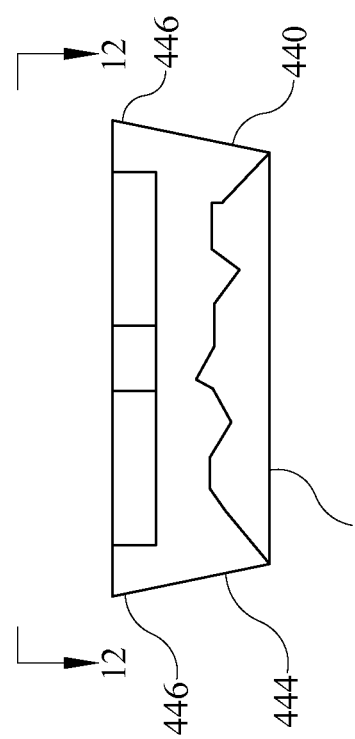
FIG. 11 is a side view of a support in accordance with one embodiment of the instant invention.

Referring now to FIGS. 10-13, central fiber portion 400 may include a plurality of creases 404 that delineate extraction region 410 from capillary portion 402 and end portion 412, so as to provide an extraction region 410 that extends outwardly through aperture 360 of lower body 300. FIGS. 11-13 depict an extraction region support 440 that, in an exemplary embodiment is comprised of a slightly compressible but elastic, waterproof, inert material such as Sanoprene®, that extends through aperture 360 and provides support and shape to extraction region 410 of fiber portion 400. Support 440 includes a pair of opposed angled side surfaces 444 that, at an upper edge 446 thereof are slightly wider than the longitudinal dimension of aperture 360. This feature of the invention 10 permits support 440 to be inserted through aperture 360 from the interior of test assembly 100 without extending entirely through aperture 360. Support 440 further includes an extraction surface 442 that is generally the same dimension as the extraction region 410 of fiber portion 400.

As seen in FIG. 3 extraction region 410 closely contacts extraction surface 442 of support 440 as both are inserted through aperture 3670 of lower body 300. When assembled support 440 is trapped or held in place between upper body 200 and lower body 300, thereby forcing extraction surface 442 and extraction region 410 through aperture 360. Once assembled the combination of support 400, extraction surface 442 and extraction region 410 provide for a consistent, repeatable contact area between extraction region 410 and surface 2 which in turn provides consistent and reliable solvent 3 flow characteristics through assembly 100. This feature of the invention ensures that test system 10 provides accurate and repeatable test results over a wide variety of surfaces, and from one test system 10 to another.

Additionally, since support layer 440 is flexible, extraction region 410 and support 440 operate in concert to assure that when extraction region 410 is in contact with a surface 2 and pressure is applied to test system 10 utilizing adhesive tape or the equivalent (not shown), extraction region 410 conforms to a plurality of surface 2 geometries while maintaining contact between extraction region 410 and surface 2. In this fashion rough, uneven, curved, flat of irregular surfaces often found in many surface testing environments, such as untreated steel, boat hulls, pipes etc. may be accurately tested since the extraction region 410 (and thus the predetermined contact area) is maintained over a broad variety of surfaces 2. The invention is therefore capable of maintaining a reproducible contact area between system 10 and surface 2 which enables the accurate determination of, for example, the concentration of a mass of contaminant in a predetermined unit area.

Figure 15:
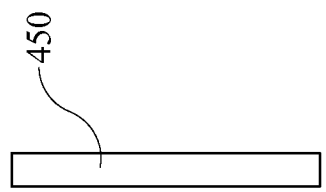
FIG. 15 is a view of a reservoir of a test patch system taken along the line 15-15 of FIG. 14 in accordance with one embodiment of the instant invention.
Figure 14:
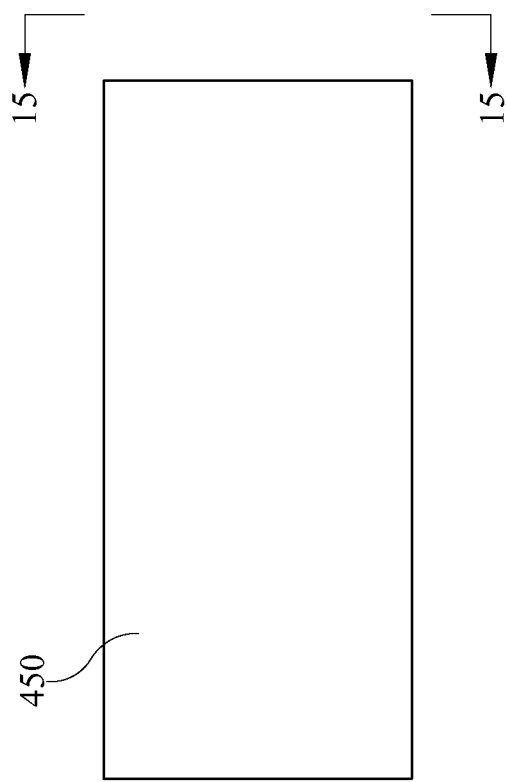
FIG. 14 is a view of a reservoir of a test patch system in accordance with one embodiment of the instant invention.
Figure 16:
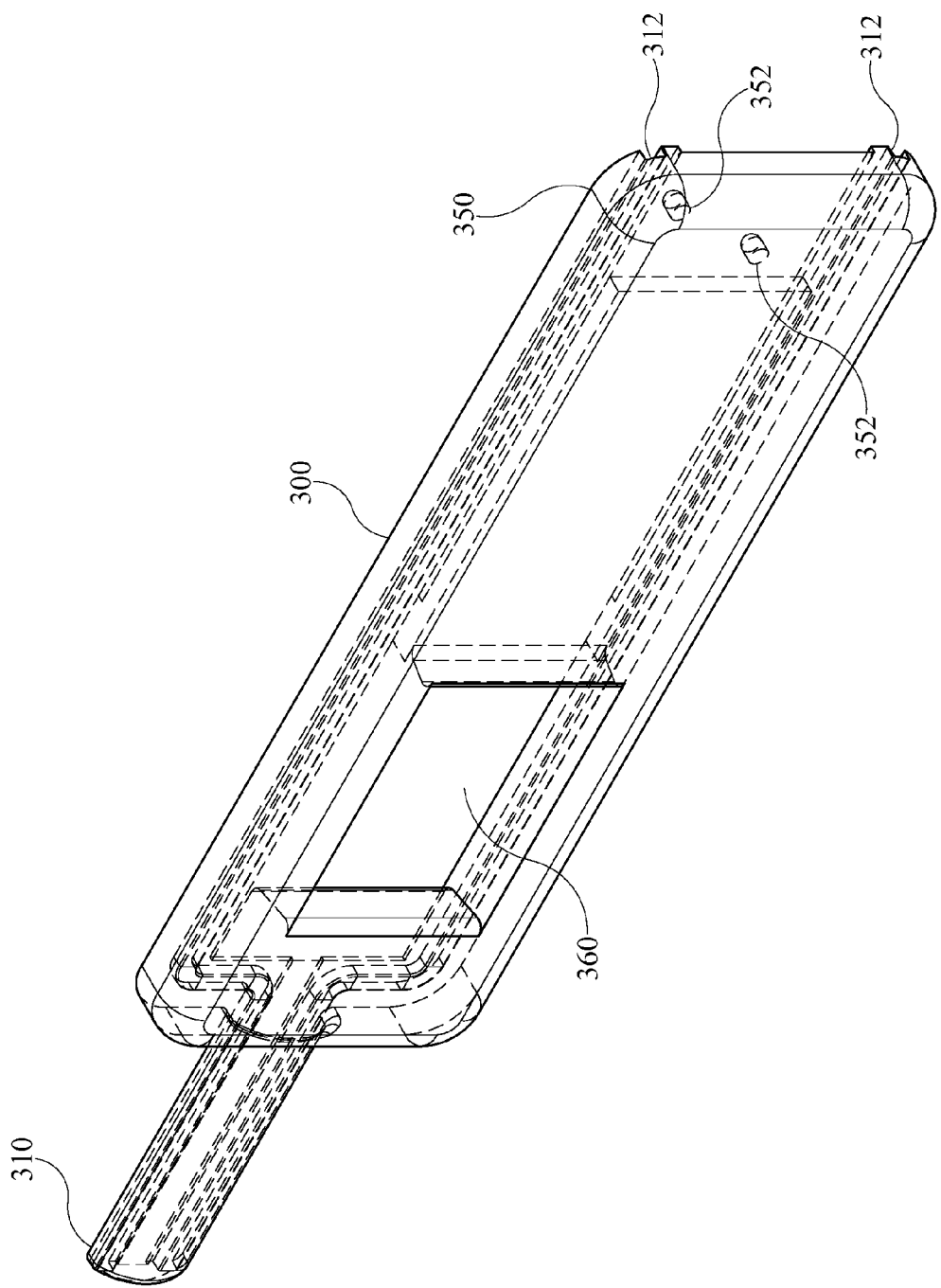
FIG. 16 is an isometric view of a lower body of a test patch system in accordance with one embodiment of the instant invention.
Figure 21:
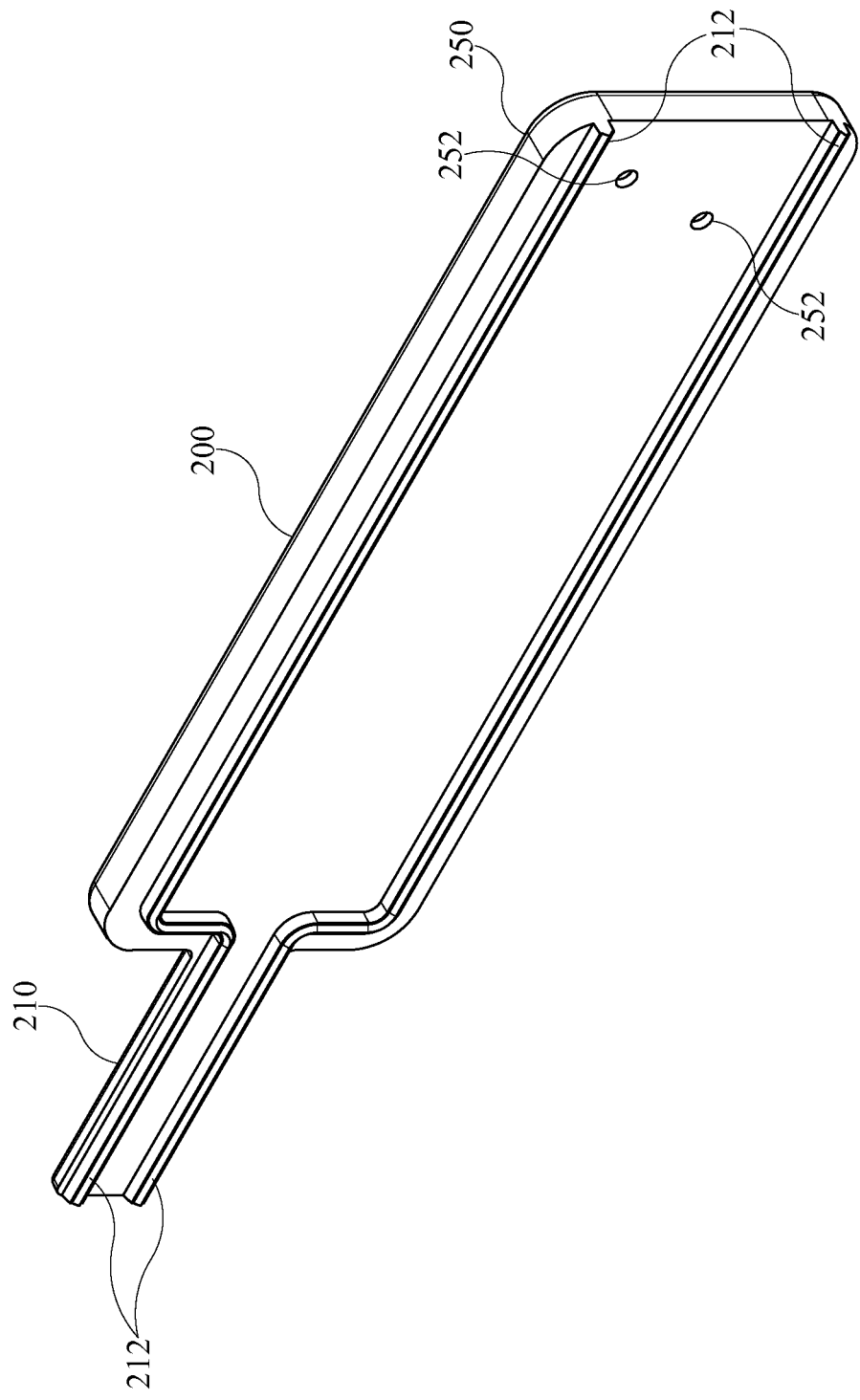
FIG. 21 is an isometric view of an upper body of a test patch system in accordance with one embodiment of the instant invention.
Figure 22:
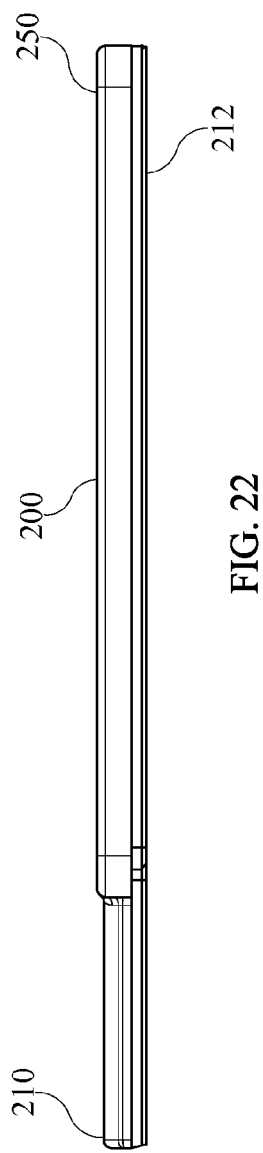
FIG. 22 is an elevation view of an upper body of a test patch system in accordance with one embodiment of the instant invention.
Figure 24:
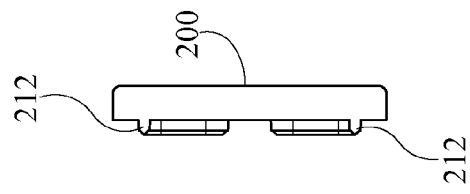
FIG. 24 is a view of an upper body of a test patch system taken along the line 24-24 of FIG. 23 in accordance with one embodiment of the instant invention.
Figure 23:
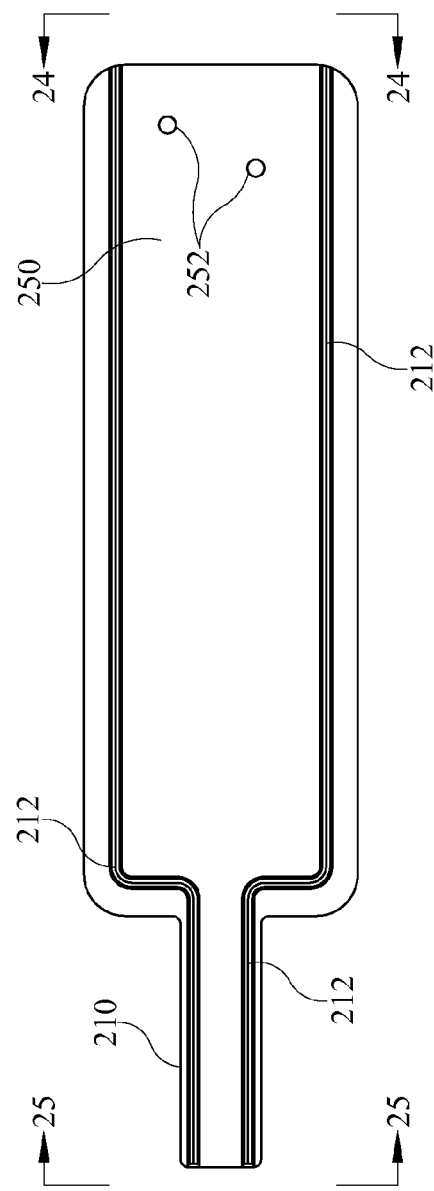
FIG. 23 is a top view of an upper body of a test patch system in accordance with one embodiment of the instant invention.
Figure 25:
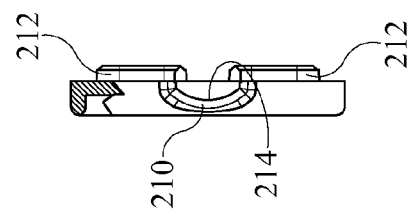
FIG. 25 is a view of an upper body of a test patch system taken along the line 25-25 of FIG. 23 in accordance with one embodiment of the instant invention.

FIGS. 14 and 15 depict a fiber reservoir 450 that may comprise an absorbent fibrous material that is positioned within reservoir 370 for collecting solvent 3 that flows from end portion 412 of fiber portion 400. Fiber reservoir 450 may comprise material similar to that of central fiber portion 400 and may also be shaped to fit generally within the volume defined by reservoir 370. As long as fiber reservoir 450 and central fiber portion 400 are not both completely saturated with solvent 3, fiber reservoir 450 and fiber portion 400 provide a defined flow path for solvent 3 through test system 10. The dimensions and surface tension properties of central fiber portion 400 and fiber reservoir 450 provide a driving force to pull solvent 3, and thus extracted salts or other constituents, out of extraction region 410 and into reservoir 370.

As best seen in FIG. 3, test system 10 is assembled by placing fiber portion 400 capillary region 402 in fluid end 310 of lower body 300 while inserting support 400 and extraction region 410 through aperture 360. Backplane 500 is then aligned with lower body 300 by placing index apertures 552 over index pins 312. Once backplane 500 is properly aligned, upper body 200 is positioned over lower body 300 using index apertures 212 and index pins 312, as well as ridges 210 and grooves 310. Upper body 200 and lower body 300 are then welded together using ultrasonic welding techniques along the perimeter thereof, excluding semi-circular sections 214, 314 and sensor ends 250, 350. It should be noted that in one embodiment of the invention electrode ends 524, and test electrode 526 extend through upper 200 and lower 300 bodies at sensor ends 250 and 350 to permit access to a meter or like device that is capable of supplying an electrical signal to electrodes 520, 522 for the purposes of testing for the presence of a constituent.

Once upper body 200 and lower body 300 are positioned together, support 400 is forced through aperture 360 a predetermined distance, thereby providing a consistent extraction region 410 surface area to contact surface 2.

While the present invention has been discussed in the context of measuring, for example, salts and the conductivity thereof on a surface 2 being tested, one of ordinary skill will recognize that a variety of printed sensors and electrodes for measuring a plurality of constituents may be employed as electrodes 520, 522 in the test system 10 of the present invention without departing from the scope thereof. As one example, a thermistor or equivalent temperature sensor may be included on substrate 510 to permit for temperature corrections of constituent data taken using the system and method of the present invention. This is particularly useful when the measurement of constituent data is temperature sensitive, or when multiple constituents are being tested.

In operation test system 10 is used by placing extraction region 410 in contact with surface 2 and securing system 10 thereto using adhesive tape or the like. Ampoule 20 is then inserted over end portion 100 of assembly 100, thereby piercing membrane 22 and causing solvent 3 to flow through capillary portion 402, into extraction region 410, and finally into fiber reservoir 450. Solvent in reservoir 450 thus contacts electrodes 520, 522, which can then be supplied with an electrical signal from a concomitant meter for reading signal strength of a signal applied to said electrodes.

While the present invention has been shown and described herein in what are considered to be the preferred embodiments thereof, illustrating the results and advantages over the prior art obtained through the present invention, the invention is not limited to those specific embodiments. Thus, the forms of the invention shown and described herein are to be taken as illustrative only and other embodiments may be selected without departing from the scope of the present invention, as set forth in the claims appended hereto.

We claim:

1. A test system for taking a sample of a constituent on a surface utilizing a fluid source comprising:
    an upper body having a fluid end and a sensor end;
    a lower body having a fluid end and a sensor end, an aperture in said lower body proximate said fluid end, and a reservoir disposed in said sensor end for collecting fluid;
    a central fiber portion disposed between said upper and lower bodies having a capillary portion for delivering said fluid to an extraction region, said capillary portion disposed in said fluid ends of said upper and lower bodies, and said extraction region extending through said aperture for contacting said surface and delivering fluid to said reservoir; and
    a central backplane disposed between said lower and upper bodies having a first end extending forward proximate said extraction region of said central fiber portion, and a sensor disposed on said backplane wherein said sensor is in contact with said reservoir of said lower body.

2. A test system for taking a sample of a constituent on a surface utilizing a fluid source as claimed in claim 1 comprising:
    a support having a surface shaped to extend tightly through said lower body aperture for forcing said extraction region through said aperture and providing a consistent extraction region in contact with said surface.

3. A test system for taking a sample of a constituent on a surface utilizing a fluid source as claimed in claim 2 wherein said support is comprised of a compressible, waterproof material for providing a consistent extraction region in contact with said surface.

4. A test system for taking a sample of a constituent on a surface utilizing a fluid source as claimed in claim 1 comprising:
    a lower body having a plurality of index pins extending therefrom; and
    an upper body having a plurality of index apertures therein for engaging said index pins, thereby aligning said upper body and said lower body.

5. A test system for taking a sample of a constituent on a surface utilizing a fluid source as claimed in claim 4 comprising:
    a central backplane having a plurality of index apertures therein for engaging said index pins, thereby aligning said upper body, said lower body, and said central backplane.

6. A test system for taking a sample of a constituent on a surface utilizing a fluid source as claimed in claim 1 wherein said sensor comprises:
    a plurality of electrodes in contact with said reservoir for applying an electrical signal thereto and determining conductivity of the fluid contained therein.

7. A test system for taking a sample of a constituent on a surface utilizing a fluid source as claimed in claim 1 wherein said sensor comprises:
    a plurality of conductive electrodes and a temperature sensor disposed on a substrate and in contact with said reservoir for applying an electrical signal thereto and determining conductivity and temperature of the fluid contained therein.

8. A test system as claimed in claim 1 comprising:
    a reservoir comprising a fiber reservoir for collecting fluid from said extraction region.

9. A test system as claimed in claim 1 comprising:
an upper body having a pair of opposed inwardly extending ridges, each proximate an outer edge of said upper body and extending substantially along the entire length thereof; and
a lower body having a pair of opposed grooves, each proximate an outer edge of said lower body and extending substantially along the entire length thereof, wherein said opposed grooves engage said opposed ridges of said upper body.

10. A test system as claimed in claim 9 wherein said upper and lower body are ultrasonically welded together and wherein said opposed inwardly extending ridges provide radio frequency radiation protection for said central fiber portion.

11. A test system as claimed in claim 1 comprising:
a central backplane having a sensor having a plurality of opposed electrodes thereon in contact with said reservoir for detecting said constituent on said surface and a second end extending out of said upper and lower bodies;
a fluid spacer in contact with and positioned proximate said second end of said central backplane having a fluid channel therein for directing fluid flow there through; and
a vent spacer positioned over said fluid spacer having a plurality of microscopic apertures therein in fluid communication with said fluid channel for providing an air vent to facilitate fluid flow through said test system while inhibiting fluid flow there through.

12. A test system as claimed in claim 11 wherein said fluid spacer comprises:
a plurality of index apertures therein for engaging said index pins of said lower body, thereby aligning said upper body, said lower body, and said central backplane.

13. A test system as claimed in claim 11 wherein said vent spacer comprises:
a plurality of index apertures therein for engaging said index pins of said lower body, thereby aligning said upper body, said lower body, and said central backplane.

14. A test system as claimed in claim 1 comprising:
a central fiber portion having a plurality of folds throughout, said folds delineating said extraction region from said capillary portion.

15. A test system as claimed in claim 3 wherein said support is comprised of an elastic material for providing a consistent extraction region in contact with said surface.

16. A test system as claimed in claim 1 wherein said central fiber portion comprises a single piece of fiber material.

17. A test system for taking a sample of a constituent on a surface utilizing a fluid source comprising:
an upper body having a fluid end and a sensor end;
a lower body having a fluid end and a sensor end, an aperture in said lower body proximate said fluid end, and a reservoir disposed in said sensor end for collecting fluid, wherein said upper and lower bodies engage to define a system interior;
a central fiber portion disposed between in said system interior having a single piece capillary portion for delivering said fluid to an extraction region, said extraction region extending through said aperture for contacting said surface and delivering fluid to said reservoir; and
a central backplane disposed said lower in said interior having a first end extending forward proximate said extraction region of said central fiber portion, and a sensor disposed on said backplane wherein said sensor is in contact with said reservoir.

* * * * *